United States Patent [19]

Chardack

[11] Patent Number: 4,957,504
[45] Date of Patent: Sep. 18, 1990

[54] IMPLANTABLE BLOOD PUMP

[76] Inventor: William M. Chardack, 547 Golfview Dr., Gulfstream, Fla. 33444

[21] Appl. No.: 278,788

[22] Filed: Dec. 2, 1988

[51] Int. Cl.⁵ .............................................. A61M 1/10
[52] U.S. Cl. .......................................... 623/3; 600/16; 600/17; 417/356; 415/912
[58] Field of Search ....................... 600/16, 17; 623/3; 417/356; 415/DIG. 3, DIG. 4

[56] References Cited

U.S. PATENT DOCUMENTS

| | | | |
|---|---|---|---|
| 3,273,506 | 8/1964 | Jamieson | 417/356 |
| 3,719,436 | 3/1973 | McFarlin | 417/356 |
| 3,853,429 | 12/1974 | Wiedenmann | 417/356 |
| 4,004,299 | 1/1977 | Runge | 623/3 |
| 4,688,998 | 8/1987 | Olsen et al. | 600/16 |
| 4,779,614 | 10/1988 | Moise | 600/16 |

FOREIGN PATENT DOCUMENTS

| | | | |
|---|---|---|---|
| 2410418 | 9/1974 | Fed. Rep. of Germany | 623/3 |
| 1061407 | 4/1954 | France | 417/356 |
| 1440821 | 6/1976 | United Kingdom | 415/DIG. 3 |

OTHER PUBLICATIONS

Hall, J. E. et al.: A pump for extracorporeal circulation. Medical Societies-New Inventions, p. 347, Feb. 14, 1959.

Primary Examiner—Randall L. Green
Assistant Examiner—Stephanie L. Iantorno
Attorney, Agent, or Firm—Hodgson Russ Andrews Woods & Goodyear

[57] ABSTRACT

An implantable blood pump (10) for providing either continuous or pulsatile blood flow to the heart. The pump includes a stator (16) having a cylindrical opening (14), an annular array (36 or 38) of electromagnets (40, 42) carried by the stator concentric with the cylindrical opening and lying in a plane transverse to the axis (26) of the opening, a bearing (28) carried by the stator and extending across the cylindrical opening, and a rotor (12) supported by the bearing for rotation about the axis of the cylindrical opening, the rotor being in the form of an Archimedes screw and having a permanent magnet (48) in its periphery which lies in the same plane as the array of electromagnets. A controller (44) is provided which is capable of causing the array of electromagnets to be sequentially energized to cause the rotor to rotate. A heart beat sensing device (50) and a rotor speed sensing device (54) may be associated with the controller so the controller may vary the rotational speed of the rotor so that the output of the pump is varied between a high ouptut synchronized with a heart beat and a low output.

9 Claims, 2 Drawing Sheets

IMPLANTABLE BLOOD PUMP

FIELD OF THE INVENTION

This invention relates generally to implantable blood pumps, and more particularly to a rotary blood pump capable of providing continuous or pulsatile blood flow to the body, the pump being of a reliable design and having power requirements that can be satisfied by presently available rechargeable batteries small enough to allow the patient to lead a normal life.

BACKGROUND OF THE INVENTION

In advanced cardiac or heart failure the output of the heart may drop from its normal resting output of about 5 liters a minute to an output approaching 2 liters of blood per minute. As output reaches this low level, the kidneys, liver, and brain become irreversibly damaged. In recent years different approaches have been used to treat irreversible cardiac failure. One approach is the removal of the heart and transplantation of a donar organ. While recipients now have a good chance of leading a normal life, obviously the supply of donor organs is limited. Artificial hearts have not been successful as permanent replacements, but have been used on a temporary basis as a "bridge" until a donor heart becomes available. Temporary partial assist devices have been used for acutely failing hearts expected to recover within a matter of days. One such partial assist design is shown in U.S. Pat. No. 4,704,121 which discloses a transarterial insertable blood pump. This device requires a drive cable which extends to the outside of the body of the patient. The pump of this design rotates at an extremely high speed. While this patent does address the problem of blood clotting, the complexities of its design detract from its reliability and additionally the high speed operation has created problems of drive cable reliability. This device also requires an external or internal purge supply, so constant replenishment of the fluid is necessary. In addition to the assist device of the above patent, a mechanical device which entirely replaces heart function has also been proposed, and one such example is shown in the Jarvik patent No. 4,173,796. This type of pump relies upon bladders shifting the blood between two chambers and also requires valves. Typically there is blood stagnation within this form of pump causing the formation of blood clots. This design is also unduly complicated because of its requirement for valves.

All prior art mechanical devices known to date have produced thrombosis and embolization in excess of that normaly produced by the body. In addition, the designs have been complicated and required bulky power supples thereby preventing a normal life.

OBJECTS AND SUMMARY OF THE INVENTION

It is an object of the present invention to provide an implantable blood pump which overcomes the disadvantages of prior art mechanical implantable blood pumps.

More specifically, it is an object of the present invention to provide an implantable blood pump which is simple, has no valves, is capable of producing from 2 to 8 liters per minute against a mean pressure head of 100 to 120 ml, minimizes clotting, does not require removal of the heart, and yet will permit the patient to lead a normal life.

It is another object of the present invention to provide an implantable blood pump which, as understood in physiology, is capable of pulsatile or continuous flow.

It is another object of the present invention to provide an implantable blood pump wherein the blood pump has only a single moving part, this being the rotor of an electromagnetic motor, the rotor being disposed within a stator which forms the pump casing, and the rotor being in the form of a helix of Archimedes screw.

In accordance with the present invention there is provided an implantable blood pump capable of providing either continuous or pulsatile blood flow to the body. The pump includes a stator having a cylindrical opening, an array of electromagnets carried by the stator, a bearing member carried by the stator and extending across the cylindrical opening, and a rotor supported by the bearing member for rotation about the axis of the cylindrical opening. The electromagnets are disposed adjacent the inner surface of the stator, concentric with and in a plane transverse to the axis of the cylindrical opening and are capable of being sequentially energized. The rotor is in the form of a helix and includes at least one permanent magnet embedded in the periphery thereof, the permanent magnet lying in the plane of the annular array of electromagnets so that when the electromagnets are sequentially energized the rotor will be caused to rotate. The surfaces of the stator and the rotor which are exposed to blood flow are constructed of biocompatible materials known to be thrombo-resistant.

The foregoing and other objects and advantages of this invention will become more apparent after a consideration of the following detailed description taken in conjunction with the accompanying drawings in which preferred form of this invention is illustrated.

DETAILED DESCRIPTION

Figure 1:
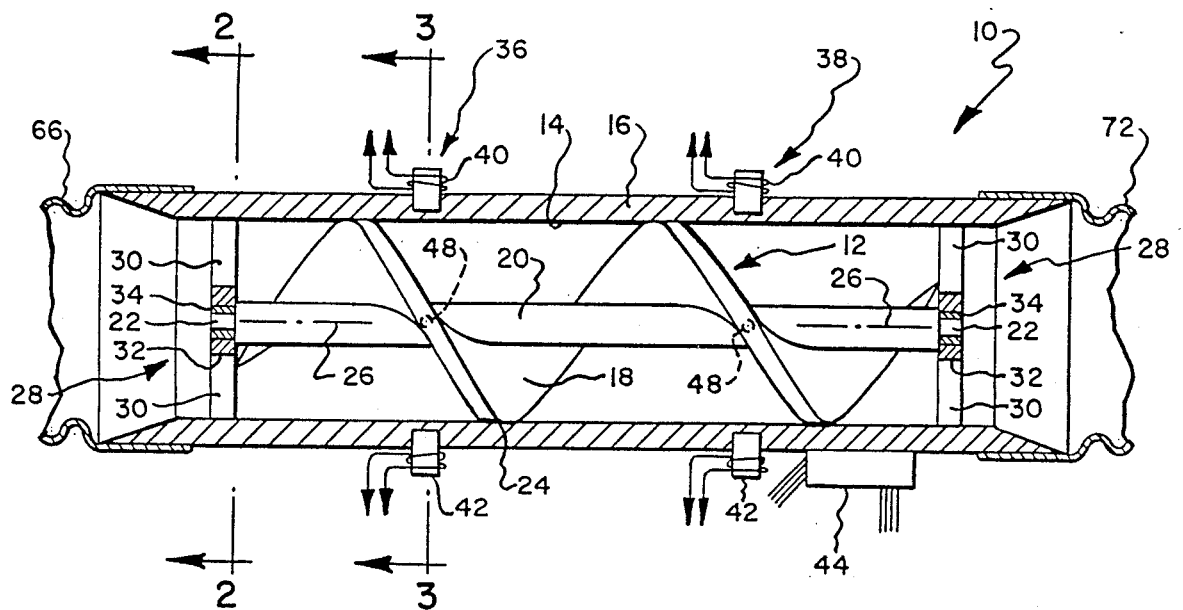
FIG. 1 is a sectional view through the implantable blood pump of this invention.
Figure 2:
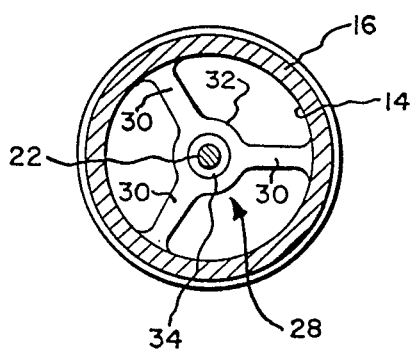
FIG. 2 is a sectional view taken generally along the line 2—2 in FIG. 1.
Figure 3:
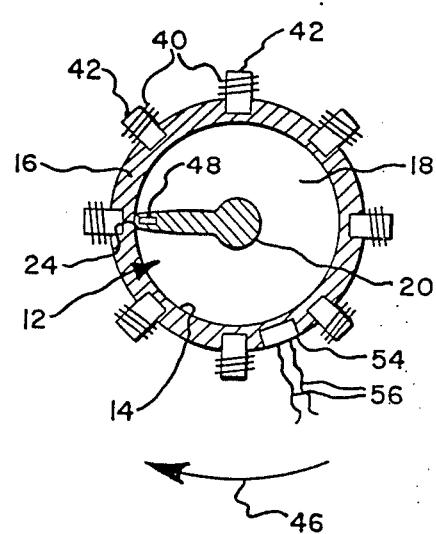
FIG. 3 is a sectional view taken generally along the line 3—3 in FIG. 1.

A section of the implantable blood pump of this invention is illustrated in FIGS. 1 through 3, the pump being indicated generally at 10. In order to increase reliability of design the pump 10 is made of the fewest possible number of moving parts as practical. As will become apparent the pump is an integral part of an electric motor, the rotor of the motor serving as the device which, when rotated, causes the flow of blood through the pump casing, the casing in turn being the motor stator. Thus, the pump consists of only one moving part, this being a rotor indicated generally at 12, the rotor being mounted for rotation within the cylindrical opening 14 of a stator 16. The rotor consists essentially of an Archimedes screw or helix 18 which is supported by a shaft 20 having reduced end portions 22. The outer peripheral surface 24 of the helix 18 lies in a cylinder generated about the axis of the shaft 20, the axis being indicated by the dot-dash line 26. While only a single flighted rotor is shown, if desirable a rotor employing more than one flight may be employed. Similarly, while only a fixed-pitch flight is shown, if desirable a variable-pitched flight or flights may be employed. The rotor is mounted in such a manner that its axis is concentric with the axis of the cylindrical opening 14, and it should be noted that the periphery 24 of the rotor is disposed close to the surface of the cylindrical opening 14. To this end, the rotor is supported by suitable bearings indicated generally at 28, which bearings are carried by the stator and extend across the cylindrical opening, there being a bearing 28 at either end of the stator 16. Each bearing 28 consists essentially of two or more radially extending arms 30, three being shown, the outer ends of which are joined with the stator, and the inner ends of the arms terminating in an annular bearing portion 32 which receives the reduced end portion 22 of the rotor 12. In the bearing shown, a reduced portion 22 at the end of the shaft 20, a step surface being formed between the reduced end portion and the shaft, which step surface may act as a thrust bearing. It may be desirable in certain situations to provide a bearing sleeve 34 within the annular portion 32 of the bearing, the bearing sleeve being formed of a suitable non-thrombogenic material. In this connection it should also be noted that all surfaces of the rotor, stator and bearings which are exposed to the blood being pumped by pump 10 are similarly formed of non-thrombogenic materials. For example, the rotor and stator may be formed of graphite covered by a very thin layer of pyrolitic carbon. Similarly, the rotor and stator could be formed of silicone modified polyurethane. Other suitable materials may be pyrolitic carbon over metal, or polished and waxed Vitallium, an alloy of chromium, by molybdenum and cobalt. The above materials are given merely as examples and applicant does not intend to be limited to such examples as other suitable non-thrombogenic materials may be used.

In a preferred design two annular arrays of electromagnets are carried by the stator, the first array being indicated generally at 36, and the second array being indicated generally at 38. Each array consists of a plurality of electromagnets which may be of any suitable design well known to those having ordinary skill in the art. Thus, as shown in the drawings, each electromagnet may be a coil 40 wrapped about a soft iron slug 42, however other forms of electromagnets may be used. Each array 36, 38, of electromagnets lies in a plane which is transverse to the axis 26 of the rotor 12. In order to properly operate the electromagnets a controller 44 in the form of a suitable electronic circuit or integrated circuit is provided, the controller being mounted upon the stator 16. The controller is suitably interconnected with the arrays of electromagnets so that each array may be sequentially operated, for example in the manner indicated by the arrow 46 in FIG. 3. Thus, with further reference to FIG. 3, the top electromagnet 40, 42 may be first energized, then the next electromagnet in the direction of the arrow 46, then each succeeding electromagnet. Each array of electromagnets cooperates with a permanent magnet 48 carried by the periphery of the rotor helix, there being a magnet disposed in the plane of each of the arrays 36, 38. Therefore, as the electromagnets of the arrays 36, 38 are sequentially energized in the direction of the arrow 46, the permanent magnets 48 will be caused to be rotated in the same direction thus driving the rotor 12. The external surface of the permanent magnets 48 are not exposed, but are in fact covered by a suitable non-thrombogenic material which is transparent to magnetic forces. When the helix 18 is rotated blood will be pumped through the pump casing or stator 16.

While the electromagnets 40, 42 and control means 44 are shown exposed to the exterior side of the stator 16, they are preferably covered. Thus, the electromagnets and controller 44 may be embedded in a suitable potting compound which is either compatible with its surroundings, or which may be covered by a material having a suitable biocompatability, such as for example a dacron mesh which would promote tissue ingrowth. Alternatively, an external cylindrical structure may be disposed about the electromagnets, as for example a sleeve having two reduced end portions. Such a sleeve could be formed of a polyurethane or silicone rubber or other materials known to be suitable for implantation in human tissue. Also, while the manner in which the coils 40 are connected to the controller 44 is not shown, it should be appreciated that any suitable connections may be utilized.

It is desirable that the closed helix 18 be made of a light weight material. By utilizing a light weight material, such as graphite covered with pyrolitic carbon, there are low inertial forces. This is particularly desirable when the rotor is to be selectively energized as when the pump is to be used to produce a pulsatile flow. When used as a pulsatile pump the pump may be accelerated from a low speed or free wheeling condition to a speed as high as approximately 1200 rpms in a very brief time interval and then be permitted to coast down to a speed of approximately 50 rpm or whatever minimum speed is necessary to prevent the blood from stagnating within the pump, thus further minimizing the possibility of clots forming within the blood. In order to properly time pulsatile blood flow it is necessary to provide heart beat sensing means and to have the maximum blood flow coincide with a heart beat. Similarly, in order to maintain a minimum blood flow to prevent the formation of blood clots. Which minimum flow blood flow may be between every other heart beat, it is necessary to provide rotor speed sensing means. The heart beat sensing means may be an EKG pick-up device 50 (Fig. 4) mounted upon any suitable location of the heart H. Alternatively, pressure or motion sensing devices may also be used to sense contractions of the heart. In any event, the heart beat sensing means will be suitably interconnected with the controller 44 by lead wires, such as that shown at 52. Various forms of rotor sensing devices may also be used, and one such rotor sensing device may be a Hall-effect sensor 54 (FIG. 3) mounted between two adjacent electromagnets 40, 42, the Hall-effect sensor in turn being interconnected with the controller 44 by suitable lead wires 56. While a Hall-effect sensor is shown, it should be appreciated that other forms of devices may be used to sense either rotational speed of the rotor or even alternatively the pump output.

By using the particular pump described above it is possible to either provide continuous blood flow where the electromagnets are sequentially operated at a constant speed or a pulsatile blood flow where the speed of the electromagnets varies to impart varying rotational speeds to the rotor. In any event, the small diameter of the pump permits such variations as may be desired, and additionally, by ensuring that the pump never comes to rest by always maintaining a suitable munimum speed, it is possible to prevent blood stagnation and, with the use of suitable non-thrombogenic materials, minimize clot formation.

Figure 4:
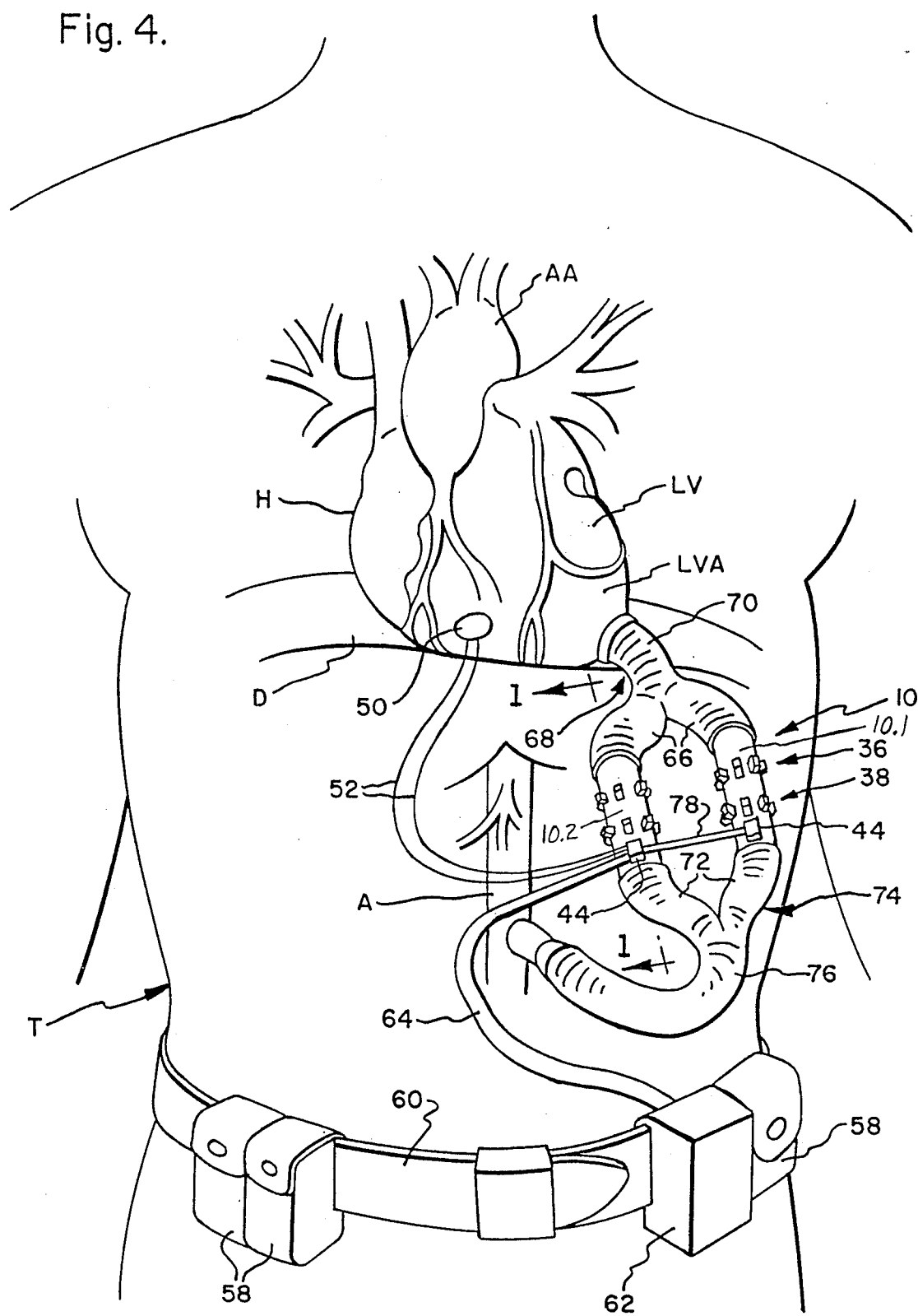
FIG. 4 is a partial view of a human torso showing the manner in which two implantable blood pumps are connected to the apex of the left ventricle at one end and the descending aorta at the other end.

As shown in FIG. 4 the pump of this invention may be powered by external rechargeable battery packs carried in pockets 58 on the belt 60. Also mounted on the belt 60 is an external controller 62 which may be utilized to adjust the operation of the internal controller 44. The controller and battery packs are interconnected with the controllers 44 by a transcutaneous port (not shown) and wiring harness 64.

Because of the relatively small size of the pump, which may be ¾-inch in diameter by 2½ inches in length, because of its ability to produce either continuous or pulsatile blood flow, and also because of its capacity which may range from 1 to 4 liters per minute per pump, the pump may be used in a number of differing applications. In addition, by merely varying the diameter of the pump or by changing the flighting of the rotor it is possible also to vary the flow range of the pump in a manner well known in the art. Therefore, while the output of the preferred pump size may range from 1 to 4 liters per minute, it is possible to substantially increase the output of a single pump up to approximately 8 liters per minute or more. In any event because of its wide flexibility the pump may be used as either a heart assist device, or for substituting for total heart action depending on the connections made to the cardiovascular system.

Referring now to FIG. 4, one application of the implantable heart pump of this invention is illustrated wherein two parallel pumps are used as a left ventricular assist device. In this view the patient's thorax is indicated by the letter T, the diaphragm by the letter D, the heart by the letter H, and the aorta by the letter A. In addition, the aortic arch is represented at AA, the left ventricle at LV, and the apex of the left ventricle at LVA. In the application shown in this figure, two pumps 10.1 and 10.2 are mounted in parallel and are used as a left ventricular assist. To this end, the inlet end of each of the two pumps is connected to the outer end of one of two branches 66 of a first bifurcated synthetic arterial prosthesis, frequently called a graft, indicated generally at 68, the outer end of the main trunk 70 of the arterial prosthesis 68 being sutured or otherwise suitably secured to the apex LVA of the left ventricle LV. The outlet ends of the two parallel pumps are in turn connected to the outer end of the branches 72 of a second bifurcated graft 74, the outer end of the trunk portion 76 being interconnected with the descending aorta A by suturing or the like below the renal artery (not indicated). The manner in which each of the pumps is connected to the branches will be apparent to those of ordinary skill in the art. The controller 44 of each of the pumps 10.1 and 10.2 will be interconnected with each other by means of a harness 78. The lead wires 52 and 56 from the heart beat sensing device 50 and the rotor speed sensing means 54 will in turn be interconnected with one of the controllers 44, but by interconnecting the controllers to each other through the harness 78, it will be possible to control each of the pumps in response to the sensed signal. In this embodiment one of the two pumps can be run continuously while the other of the two pumps can be operated as a pulsatile pump in response to heart beats. Alternatively, both pumps could be run as pulsatile pumps, continuous pumps, or the pumps could alternate between pulsatile peak output and continuous flow. For example, pump 10.1 can be run up to a pulsatile pump peak output of say approximately 1200 rpms during a first heart beat, be permitted to coast down to a continuous flow operating range of approximately 400 rpms during a second heart beat, and then be run up to a pulsatile peak output of approximately 1200 rpm during a third heart beat, and so on. Meanwhile, the other pump 10.2 can start out initially at a continuous flow speed of approximately 400 rpm during the first heart beat, then be run up to pulsatile peak speed of approximately 1200 rpm during the second heart beat, and then be permitted to coast down to continuous flow speed of approximately 400 rpm during a third heart beat, and so on. In this way the load is constantly switched between the two pumps, and pulsatile flow is achieved. By discharging into the descending aorta below the renal arteries there is less potential chance of injury to the patient due to the formation of very small blood clots as the circulatory system below the renal artery is capable of dissolving small clots which are formed during normal circulation. Bifurcated arterial prosthesis are well known in the art and one such arterial prosthesis is the aorta-femoral arterial prosthesis. Other suitable arterial prosthesis may be employed or developed.

While a novel parallel pump application is shown, it may be desirable to use the pumps 10 in other arrangements. For example, total heart function may be achieved where the left ventricle is interconnected with the aorta arch by one or more pumps and the right ventricle is interconnected with another pump for discharge to the pulmonary artery. Instead of connecting to a ventricle an auricle may be tapped. Alternatively, as an assist device only a single pump may be utilized to connect the apex of the left ventricle to the aorta. Other applications of the implantable blood pump of this design will be apparent to those of ordinary skill in the art. While the pumps are shown below the diaphragm D in FIG. 4, one or more pumps may be disposed above the diaphragm, with all connections being above the diaphragm.

The above pump design, which is very simple in construction, avoids the pitfalls of bladder type devices which have been associated with clotting and emboli. In addition, the present device does not require any valves and is of a very simple design. The pump 10, depending upon the manner in which it is energized, can provide either continuous flow or a pulsatile flow. In addition it is possible to achieve both pulsatile or continuous flow. As the capacity of the pump can be increased by simply increasing its diameter, say for example from three quarters of an inch to one inch, the flow can be varied from a partial assist to a total assist.

It should be noted that while in this description the power supply is connected to the pump by a cable fed through a transcutaneous port it is also possible to transmit electrical power from an externally located coil to a subcutaneously implanted coil, thus avoiding all transcutaneous pathways. Also, the internal controller(s) 44 may be reprogrammed by radio frequency signals through intact skin rather than by harness 64.

While a preferred structure in which the principles of the present invention have been incorporated is shown and described above, it is to be understood that this invention is not to be limited to the particular details shown and described above, but that, in fact, widely differing means may be employed in the broader aspects of this invention.

What is claimed is:

1. An implantable and biocompatible blood pump capable of providing either continuous or pulsatile blood flow, the pump comprising:
    a stator having a cylindrical opening;
    bearing means carried by the stator and extending across the cylindrical opening;
    a rotor supported by the bearing means for rotation about the axis of the cylindrical opening, the rotor being in the form of a helix; and
    electromagnetic means carried by the stator for driving the rotor.

2. The pump as set forth in claim 1, wherein a permanent magnet is embedded in the periphery of the rotor and the electromagnetic means is an annular array of electromagnets carried by the stator and concentric with the axis of the cylindrical opening, the array lying in a plane transverse to the axis of the cylindrical opening, which plane passes through the permanent magnet carried by the rotor, and wherein the electromagnets are capable of being sequentially energized.

3. The pump as set forth in claim 2 wherein a second annular array of electromagnets is carried by the stator in a second plane parallel to the first plane, there being a second permanent magnet carried by the rotor and lying in the plane of the second array of electromagnets.

4. The pump set forth in claim 1 wherein the helix is closed.

5. The pump as set forth in claim 1 wherein the bearing means are disposed at both ends of the cylindrical opening, opposite ends of the helix being supported by the bearing means.

6. The pump as set forth in claim 1 wherein all surfaces of the stator, rotor, and bearing which are exposed to the blood being pumped are made of non-thrombogenic materials.

7. The pump as set forth in claim 1 further comprising control means interconnected with the electromagnetic means and capable of operating the electromagnetic means in such a manner that the rotor is driven at varying speeds.

8. The pump as set forth in claim 7 further comprising heart beat sensing means capable of sensing a heart beat, the heart beat sensing means being interconnected with the control means, the control means being capable of increasing the output of the pump in sychronism with the heart beat.

9. The pump as set forth in claim 8 further comprising rotor sensing means capable of sensing the rotational speed of the rotor, said control means additionally being interconnected with the rotor sensing means and said control means being capable of ensuring that the rotor will be rotated at all times to ensure that blood within the pump is always in motion and does not stagnate.

* * * * *